United States Patent [19]

Shilling et al.

[11] Patent Number: 5,176,630

[45] Date of Patent: Jan. 5, 1993

[54] RECTAL INSERTION DEVICE AND CONTROL VALVE MEANS THEREFOR

[75] Inventors: Thomas Shilling, Aurora; Alan R. Lee, Littleton, both of Colo.

[73] Assignee: Aegis Medical, Inc., Littleton, Colo.

[21] Appl. No.: 572,034

[22] Filed: Aug. 23, 1990

Related U.S. Application Data

[63] Continuation-in-part of Ser. No. 247,736, Sep. 22, 1988, abandoned.

[51] Int. Cl.⁵ .............................................. A61M 3/02
[52] U.S. Cl. ...................................... 604/41; 604/275
[58] Field of Search ..................... 604/27–36, 604/39, 41, 43, 48, 54, 113, 114–118, 131, 151, 257–264, 275–280, 96–103; 606/191, 192; 600/29; 128/750, DIG. 12

[56] References Cited

U.S. PATENT DOCUMENTS

| | | | |
|---|---|---|---|
| 429,374 | 6/1890 | Charlesworth | 604/276 |
| 1,518,211 | 12/1924 | Maue | 604/275 |
| 1,710,701 | 4/1929 | Hertzberg | 604/41 |
| 1,853,202 | 4/1932 | Catlin | 604/32 |
| 2,583,298 | 1/1952 | Kowan | 604/276 |
| 3,734,100 | 5/1973 | Walker et al. | 128/207.15 |
| 4,874,363 | 10/1989 | Abell | 604/276 |

FOREIGN PATENT DOCUMENTS

| | | | |
|---|---|---|---|
| 67672 | 8/1892 | Fed. Rep. of Germany | 604/278 |
| 20821 | of 1895 | United Kingdom | 604/278 |

Primary Examiner—C. Fred Rosenbaum
Assistant Examiner—William W. Lewis
Attorney, Agent, or Firm—John E. Reilly

[57] ABSTRACT

A colonic lavage apparatus including a speculum (12) in which the speculum (12) takes the form of an elongated tubular body (29) having a tapered leading end (30) provided with a pair of diametrically opposed apertures (36). The major length of the body (29) tapers rearwardly from the leading end (30) into a trailing end (45) which is coupled to a liquid delivery line (L) from a source of liquid under pressure. A control line (L') is coupled to a valve assembly (16) at an opposite end of the speculum (12) to that of the delivery line (L), the valve assembly (16) including an elastic tubular liner (28) and a pressure port (24) positioned on an external surface of the valve (16) which is in communication with the source of liquid under pressure, the valve (16) being opened and closed in response to the differential pressure between the liquid in the pressure port (24) and the speculum (12). The speculum (12) may be provided with an inflatable cuff (72) and means for inflating the cuff (72) in order to hold the speculum (12) in the anal canal of a patient.

13 Claims, 2 Drawing Sheets

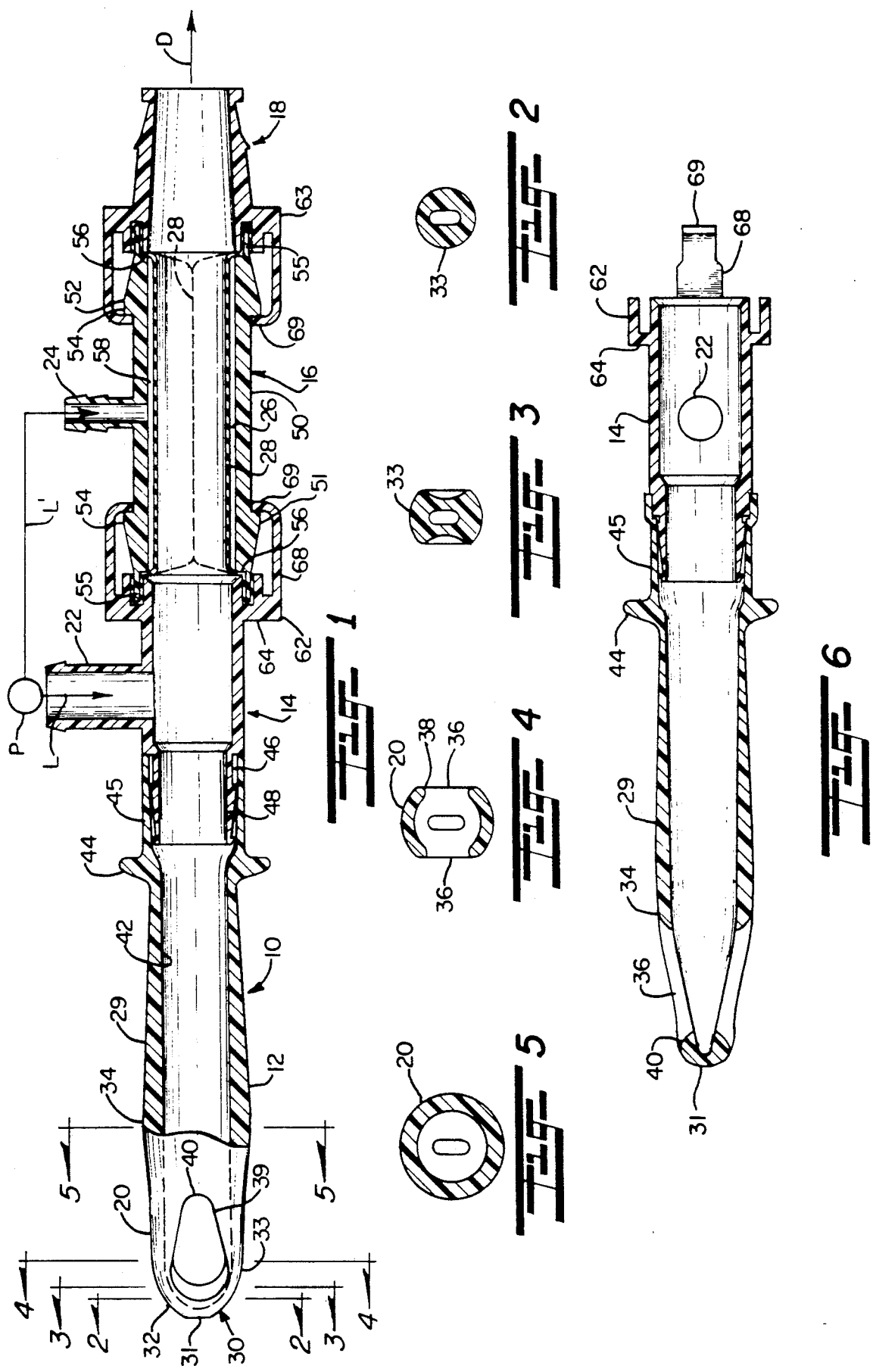

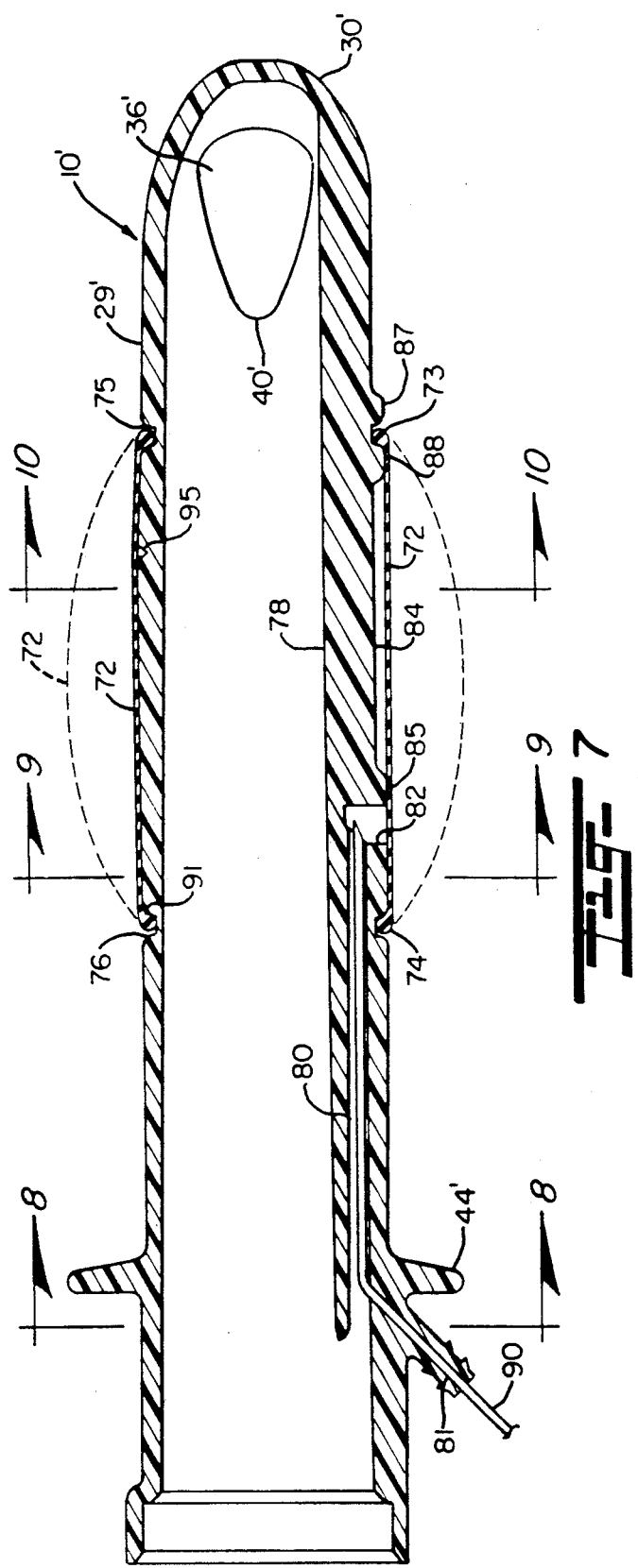

5,176,630

RECTAL INSERTION DEVICE AND CONTROL VALVE MEANS THEREFOR

CROSS-REFERENCE TO RELATED APPLICATION

This application is a continuation-in-part of Ser. No. 247,736 for RECTAL INSERTION DEVICE AND CONTROL VALVE MEANS THEREFOR, filed Sep. 22, 1988 now abandoned, by Thomas Shilling and Alan R. Lee.

This invention relates to rectal insertion tubes; and more particularly relates to a novel and improved speculum and control valve in regulating the delivery to and removal of liquids from the rectum.

BACKGROUND AND FIELD OF INVENTION

The rectum is a very delicate part of the human body and, as such, requires that it be protected from abrasion, perforation, infection as well as excessive pressure. Accordingly, any device which is intended for rectal insertion should not have any tendency to perforate the rectal wall even in coming into contact with the wall during insertion, must not have sharp contacting edges, and must open the anal sphincter as evenly as possible with the support of maximum circumference of dilation and at a rate which is initially high and gradually reduces to a low rate as dilution reaches a maximum. In the use of a speculum which is intended for the delivery of liquid into the rectum, it is important that water or liquid flow not be concentrated at any spot on the mucosa of the anal canal and which would tend to constantly traumatize an area in the immediate vicinity of the operating position. Further, the speculum should offer the maximum possible aperture for free flow to minimize back pressure during moments of peristalsis. It is also desirable that the speculum be biased so as to be drawn into the rectum under anal contraction and include an anal ring or stop to regulate penetration depth as well as prevent leakage during use.

Various different types and designs of rectal tubes have been devised in the past. For example, U.S. Pat. No. 1,198,742 to C. W. Meinecke discloses a double-ended tubular retainer system to which a discharge tip and inlet may be added. However, the portion which is intended for insertion into the anal canal is a straight parallel tube with offset apertures or openings through which a saline solution is to be discharged. U.S. Pat. No. 1,853,202 to D. B. Catlin similarly employs a relatively straight tube with a gradual forward taper at the leading end. The device is made of a rigid sterilizable material and includes a three-way valve which is manually controlled to determine direction of flow. In U.S. Pat. No. 1,710,701 to H. Hertzberg, an insert tube has a leading, gradually tapered forward tip which forms a solid end of a generally tubular body, the body also being gradually tapered in a forward direction and having forwardly tapered, diametrically opposed apertures or openings which are large enough to permit the passage of liquid as well as solid waste matter. In addition, a shoulder is formed at the trailing end of the tube to limit the depth of penetration into the anal canal. For irrigating purposes, a flexible hose extends from an elevated water bag into the trailing end of the speculum for delivery of water under pressure into the rectum and a drain line is manually closed off by doubling it upon itself during the injection of water. In order to discharge the water from the colon, a larger opening or drain line is opened so as to permit the removal of water and any fecal matter dislodged from the intestinal tract. Nevertheless, the above and other similar types of rectum insertion devices fail to eliminate the possibility of occluding the aperture of the speculum eye thereby causing undue pulling on the mucosa during the drain interval so as to insure the most complete and total elimination as possible as would normally occur during a bowel movement. Other important considerations have to do with the proper dilation of the anal canal during insertion of the speculum followed by anal contraction to effectively lock the speculum in place, proper orientation with respect to the rectum, and at the same time limiting its depth of penetration.

In applicants' copending patent application corresponding to U.S. Ser. No. 247,734 filed Sep. 22, 1988, for "BOWEL CARE APPARATUS", there is set forth and described a novel and improved system for colonic lavage in which a pump circuit is provided to deliver water from a fill receptacle under pressure through a fill line and speculum into the colon, there being a drain line extending away from the speculum and a valve in the drain line which is movable to a closed position when water pressure in the pump exceeds the water pressure in the speculum and to an open position when the water pressure in the speculum exceeds that in the pump.

SUMMARY OF THE INVENTION

According to a first aspect of the present invention there is provided a colonic lavage apparatus including a speculum for insertion into the anal canal of a patient wherein the speculum comprises an elongated tubular body having a hollow interior and terminating at one end in a tapered leading end and at an opposite end in a tubular trailing end, said body having a maximum diameter area adjacent to but rearwardly of said tapered leading end and a portion tapering rearwardly from said maximum diameter area, said tapered leading end being provided with at least one aperture communicating with the interior of said body, each said aperture diverging forwardly and having rounded edges surrounding said aperture, and an anal stop adjacent said trailing end of said body.

According to a second aspect of the present invention there is provided a colonic lavage apparatus including a speculum for insertion into the anal canal of a patient wherein the speculum comprises an elongated tubular body having a hollow interior and terminating at one end in a tapered leading end and at an opposite end in a tubular trailing end, said body having a maximum diameter area adjacent to but rearwardly of said tapered leading end and a portion tapering rearwardly from said maximum diameter area, an inflatable cuff disposed in surrounding relation to said portion of said body tapering rearwardly from said maximum diameter area, and means communicating with the interior of said cuff for inflating said cuff to expand in an outward circumferential direction away from said body, the cuff having a differential thickness increasing from a forward end engaging a groove in said body to an opposite rearward end engaging a second groove in said body axially spaced from said first groove.

According to a third aspect of the present invention there is provided a colonic lavage apparatus including a speculum for insertion into the anal canal of a patient wherein the speculum comprises an elongated tubular body having a hollow interior and terminating at one end in a tapered leading end and at an opposite end in a tubular trailing end, said body having a maximum diameter area adjacent to but rearwardly of said tapered leading end and a portion tapering rearwardly from said maximum diameter area, an inflatable cuff disposed in surrounding relation to said portion of said body tapering rearwardly from said maximum diameter area, and means communicating with the interior of said cuff for inflating said cuff to expand in an outward circumferential direction away from said body, the cuff being composed of elastomeric material and of tubular configuration having a pair of opposite ends, said opposite ends of said cuff being disposed in snug-fitting, sealed engagement with axially spaced grooves in said body.

According to a fourth aspect of the present invention there is provided a colonic lavage apparatus including a speculum for insertion into the anal canal of a patient, and a control valve interconnected between said speculum and a drain line, the control valve comprising an outer relatively inflexible tubular conduit having an inner diameter, one end of said tubular conduit being connected to said speculum and an opposite end being connected to an end of said drain line, an elastic tubular liner inserted within and coextensive with said tubular conduit, said flexible liner having a diameter substantially corresponding to the inner diameter of said tubular conduit, connecting means for connecting opposite ends of said flexible liner to said one end and said opposite end of said tubular conduit, a control port in a wall of said tubular conduit intermediate of said opposite ends of said flexible liner and in communication with an annular space in surrounding relation to said liner, and means for supplying fluid under pressure to said speculum and said control port thereby opening and closing said liner in response to the differential pressure between the liquid in said control port and the interior of said speculum.

Other objects, advantages and features of the present invention will become more readily appreciated and understood when taken together with the following detailed description in conjunction with the accompanying drawings, in which:

BRIEF DESCRIPTION OF THE DRAWINGS

FIG. 1 is a longitudinal section view of a preferred form of speculum and valve unit in accordance with the present invention;

FIG. 2 is a cross-sectional view taken about lines 2—2 of FIG. 1;

FIG. 3 is a cross-sectional view taken about lines 3—3 of FIG. 1;

FIG. 4 is a cross-sectional view taken about lines 4—4 of FIG. 1;

FIG. 5 is a cross-sectional view taken about lines 5—5 of FIG. 1;

FIG. 6 is a longitudinal section view of the preferred form of speculum taken at right angles to the section view of FIG. 1;

FIG. 7 is a longitudinal sectional view of a second embodiment of a speculum in accordance with the present invention having an inflatable cuff;

FIG. 8 is a cross-sectional view taken along lines 8—8 of FIG. 7;

FIG. 9 is a cross-sectional view taken along lines 9—9 of FIG. 7; and

FIG. 10 is a cross-sectional view taken along lines 10—10 of FIG. 7.

DETAILED DESCRIPTION OF THE PREFERRED EMBODIMENT

Referring in more detail to the drawings, a first embodiment of a colonic lavage apparatus 10 is broadly comprised of a speculum 12, T-shaped fitting 14, a liner valve 16, and a coupling 18. The elements 12, 14, 16 and 18 are assembled together in fixed, end-to-end, coaxial relation to one another and are of progressively increasing diameter from a forward or leading end 20 of the speculum through the valve coupling end portion 18 so as to present an unobstructed passage for flow of liquid and solid materials therethrough. As a setting for the present invention, the speculum and valve assembly will be described as forming a part of a colonic lavage apparatus in which a liquid fill or delivery line represented at L is affixed to inlet port or fitting 22 which forms the stem of the T-shaped fitting 14 and a pressure control line L' is connectable to pressure port or fitting 24 on the control valve 16; and further, a drain line D is connectable to coupling end portion 18. In this setting, the speculum is intended for insertion into the anal canal of a patient and water is delivered under pressure from a pump P or other source of water under pressure via inlet port 22 through the speculum into the rectum or colon area of a patient. The fluid delivered via line L' and pressure port 24 is at the pressure level of the same pump P that delivers water under pressure to the port 22. However, by virtue of the free flow of water through the speculum into the colon area, as opposed to the flow of fluid through pressure port 24 into a confined annular space 26 in surrounding relation to a flexible or elastomeric liner 28, the differential pressure is such that it will cause the liner to be constricted into a closed position, as shown in dotted form in Figure 1, whereby to close the valve and confine the flow of water through the pressure port 22 and speculum 12 into the colon.

At the end of a fill interval and upon interruption in the flow of water through the inlet port 22 and the pressure port 24, the hydrostatic head of water in the patient is sufficient to flow outwardly through the speculum together with waste matter thereby to open the valve 16 by expansion or dilation of the liner 28 for return flow through the valve and into the drain line D. Although not shown, check valves are provided in the fill line L connected to the inlet port to prevent return flow of water from the speculum therethrough.

The construction and arrangement of the speculum 12 will now be described illustrating how access is obtained through the anal canal to the central axis of the open inside diameter of the rectum, referred to as "centration to the rectal lumen". The speculum 12 has an elongated thinwalled tubular body 29. In the preferred form of speculum, the leading end 20 terminates in a rounded, snub-nosed tip 30 having a flattened end surface 31 of circular configuration at the very apex of the speculum and a generally elliptical surface portion 32 which is formed by the rotation of a displaced conic section taken as a quadrant of an ellipse located with displacement about the longitudinal axis of the speculum 12. The surface 32 merges into a more gradually tapered surface 33 which is relatively straight-walled and diverges outwardly and rearwardly to a circumferential crown portion 34 which defines the maximum diameter of the speculum 12. A pair of diametrically opposed eyelets or apertures 36 are formed through the wall thickness of the speculum, each having a diameter taken laterally which is the diameter of the forwardmost portion of the central inside diameter of the speculum at the area 34. A diameter which has proven to be most effective in evacuating the colon is on the order of 0.550″ to 0.700″. Larger diameters tend to drain too swiftly and create a suction upon the mucosa while smaller diameters tend to clog with waste matter. Location of the eyelets near the tip of the speculum is important to achieve alignment of the eye of the speculum with the center of the inside diameter of the rectum and minimizes occlusion of the eyelets, which otherwise may cause undue pulling on the mucosa during the drain cycle, and better assure complete and total elimination of the waste material from the rectum. Accordingly, each eyelet 36 includes a generally semi-circular forward opening portion 38 and a rearward portion which diverges along inclined walls 39 from a rearwardmost arcuate portion 40. The eyelets are formed symmetrically with respect to the circumference of the leading end 20 and each is provided with rounded edges which are flared or ramped outwardly away from the inner diameter of the speculum into the outer diameter, for example, as illustrated at 40 in FIG. 6.

It will be noted from FIG. 1 that the tubular body 29 has an inner wall surface 42, and the leading end similarly is formed with an inner wall surface of uniform diameter which forms an uninterrupted continuation of the inner wall surface 42 until it converges into the rounded tip area 30, as illustrated in dotted form in FIG. 1. However, the external wall surface of the body increases in thickness throughout the leading end to the maximum diameter 34, then is gradually tapered in a rearward direction until its termination in an anal stop ring 44 which is in the form of a collar in external surrounding relation to the rearward end of the body. A connecting end portion 45 forms a tubular, slightly enlarged axial continuation of the body 29. Connection of the speculum 12 to another device may be accomplished by pressfit insertion of a barbed end portion, such as, end portion 48 of the T-shaped fitting 14, the end portion provided with external ribs or barbs 49 which interengage with ribbed elements 46 on the internal diameter of the connecting end portion 45. Suitable interlocking keys and keyways between the coupling end portions, not shown, may be provided to assure proper orientation of the speculum and its eyelets 36 with respect to the fitting 14 and the control valve 16.

When the speculum is to be inserted into the anal canal of a patient, the tip 30 and its flattened end surface 31 is intended to prevent perforation of the mucosa lining of the rectum which lies exactly opposite and perpendicular to the anal canal. When the speculum is inserted, there is the likelihood of crossing over the inside diameter of the rectum into contact with the delicate mucosa lining of the rectal wall. The elliptical surface 32 is the initial part of the speculum which enters into the anal orifice by plying open the external sphincter, traversing the anal canal and then opening the internal sphincter. This type of dilation is made possible by virtue of the variable rate of opening of the sphincter muscles which the ellipse establishes with a rapid initial entry and progressively slower as the sphincter muscle is stretched until arriving at full dilation. The rounded edges of the eyelets 36 minimize the possibility of pulling down or snagging hemorhoids by the speculum during removal at the end of a procedure. The forward rotation of the eyelets 36 require that some dilation occur during insertion of the speculum and hence the requirement to make the rounded edges flare outwardly as at 40 from a point near the tip of the speculum to the full diameter of the speculum body where the leading end surface 20 intersects the maximum diameter 34. Further dilation of the internal and external sphincters of the rectum is required in order to properly utilize a tapered anal lock created by the expansion into the maximum diameter area 34 followed by gradual taper along the body 29. Here, the tension of the inner and outer sphincters of the anal orifice tend to advance the speculum inwardly along the anal canal until interrupted by the anal ring 44, and the ring 44 also serves to prevent leakage by virtue of the increased tension of the internal sphincter on the larger end of the body.

The construction of the control valve 16 provided in close proximity to the speculum 12 will now also be described. The main body of the valve is defined by an outer thick-walled, rigid conduit or tube 50 having corresponding connecting end portions 51 and 52 at opposite ends thereof. Each of the connecting end portions 51 and 52 includes an external rib 54 diverging rearwardly from a relatively thin-walled end cap 55 which extends from an internal shoulder 56. The internal surface 58 of the tube 50 is of uniform diameter between the shoulders 56, and the pressure port 24 extends through the wall of the tube into communication with the hollow interior of the tube at a point intermediately of the connecting ends 51 and 52. The liner 28 is composed of a thin-walled elastomeric material and may be a rubber or rubber-like material customarily employed in surgical tubes. In colonic lavage operations as described, the liner has a thickness on the order of 0.010″ and is sized such that its outer diameter corresponds to the inner diameter 58 of the tube 50. Opposite ends 60 of the tubular liner 28 extend beyond the end caps 55 and are expanded and reversed upon themselves so as to be doubled over the end caps 55. When released, the ends will effect tightfitting sealed engagement with the external surfaces of the end caps 55 whereby to form the sealed annular space 26 between the inner diameter 58 of the tube 50 and the liner.

Complete sealing of the ends 60 of the liner is assured by the utilization of coupling portions 62 and 63, the coupling portion 62 formed at one end of the fitting 14 opposite the barbed end 48 and the coupling 63 formed at one end of the barbed connecting end portion 18 for the drain line. Each coupling 62 and 63 includes an external circumferential shoulder 64 which extends radially outwardly from tubular end 15 of the fitting 14, and the shoulder or collar 64 is provided with an annular groove 66 in facing relation to the end cap 55 of the valve body 50 and is sized to require close-fitting insertion of the end cap 55 and the surrounding end 60 of the liner 28 into the groove. Elongated spring arms or detents 68 are disposed in circumferentially spaced relation for extension in an axial direction away from the outer surface of the collar 62, each terminating in a radially inwardly directed end 69. The detents 68 possess limited resiliency so that when the end cap 55 is inserted into the groove 66, the ends 69 will have passed over the ribbed portion 54 and into snapfit engagement with the radial shoulder at the end of the rib. The coupling portion 63 is correspondingly formed to that of the coupling 62, and like parts are correspondingly enumerated.

It will be evident that the only movable or functional part of the valve is the elastic liner 28 and which, by virtue of its elasticity, is capable of movement between an open position, as shown in full, and a closed position, as shown dotted in FIG. 1. Specifically, when pressure in the port 24 exceeds that from the speculum the liner 28 is caused to collapse inwardly along its substantial length as illustrated so as to effect a complete closure. Again, when the pressure acting against the interior of the liner 28 exceeds that in the pressure port 24, the liner will return to the expanded, open position so that the liquid and waste matter are free to pass unobstructed from the colon area through the speculum 12 and valve 16. The connecting end 18 is inserted into a drain hose D of appropriate diameter to permit removal of the liquid and waste matter into a suitable receptacle, for example, in the manner described in said copending application Ser. No. 247,734 for "BOWEL CARE APPARATUS".

In a colonic lavage operation, the ports 22 and 24 are placed under pressure during the fill cycle with the pressure at the port 24 slightly higher than that in the port 22 so that the liner 28 is caused to collapse and close the drain line. Accordingly, fresh water is pumped under pressure from the pump P via the speculum 12 and into the colon. When the pump P is turned off at the end of the fill cycle, the water pressure in the ports 22 and 24 will return to zero or atmospheric pressure with the result that liquid and waste matter from the speculum 12 are at a higher pressure and will open the valve 16 so as to be free to travel unobstructed through the valve 16 and drain line D. Preferably, the sequential fill and drain operations or cycles are controlled by a timer and can be repeated any number of times as required to effect complete removal of waste matter from the colon. It will be appreciated that the speculum is conformable for use in other applications requiring injection or delivery of a liquid into or from the rectum; also, that the control valve assembly 16 is readily adaptable for use in various applications which require an on-off valve sensitive to changes in differential pressure to automatically open and close in response to such changes.

In a second embodiment of the speculum illustrated in FIGS. 7 to 10, those parts and elements corresponding to FIGS. 1 to 6 are correspondingly enumerated with prime numerals. In the second embodiment, an inflatable cuff 72 is composed of a thin, elastomeric material and is of tubular configuration having reinfoced ends 73 and 74 in the form of 0-rings at opposite ends thereof which fit into axially spaced circumferentially extending grooves 75 and 76, respectively, in the external wall of the speculum 10'. The forwardmost groove 75 is located just rearwardly of the eyelets 36'. In addition, the body 29' includes a thickened longitudinally extending section 78 with a longitudinally extending air passageway 80 which communicates with a barbed air delivery port 81 at the rearwardmost end of the body 29'. The air passageway 80 communicates with a recessed area 82 which opens outwardly through the external surface of the body 29' at a location intermediately of the ends of the cuff 72.

The external surface of the body 29' is provided with a flatted area 84 which extends forwardly from the recessed area 82 toward the ip 30' merely to avoid or minimize warpage when using a mechanical core in the formation of the body. In addition, an external shoulder 85 is formed at the trailing edge of the flatted area 84, and spaced shoulders 87 and 88 project outwardly in a radial direction from the flatted area to define a circumferential extension of the groove 75 across the flatted area.

An air delivery line 90 extends through the air delivery port 81 and along the passageway 80 to permit delivery of air under pressure into the area beneath the cuff for the purpose of inflating the cuff to an expanded size, as shown dotted in FIG. 7.

Preferably, the cuff 72 is composed of a latex material and the reinforced ends 73 and 74 are formed by rolling opposite ends of the latex into a circular configuration so that in carrying will effectively define 0-rings which remain in sealed engagement with the grooves 75 and 76 when the cuff is inflated.

Referring to each of the grooves 75 and 76, each has an inner wall surface 90 and 91, respectively, which is relieved or beveled so that the reinforced ends 73 and 74 are tightly seated within the grooves and the wall of the cuff 72 will lay snugly against the external wall surface of the body 29' except along the flatted area 84. When the cuff is inflated, it will expand or lift off of the external surface of the body so as to expose the reinforced ends 73 and 74 to the air pressure contained within the cuff. A notched area 95 in the external surface of the body will aid in uniform distribution of air around the circumference of the cuff. At the onset of inflation, the air is completely contained and sealed within the cuff and is a combination of the reinforced ends 73 and 74 being seated in the groove 75 and 76 as well as the greater length of the cuff lying on the edges of the sidewalls of the grooves 75 and 76. As the cuff is inflated to a pressure predetermined to be a desirable maximum, the reinforced ends 73 and 74 will gradually yield to any excessive pressure so as to permit any excess air under pressure to escape by expansion of the ends 73, 74 away from sealed engagement with their respective grooves.

The cuff is preferably dimensioned to be of a length corresponding to that of the anal canal and is given a differential thickness so as to gradually increase from the forward end engaging the groove 75 to the rearward end 76 so that the cuff will more rapidly inflate or expand for the front than the rear so as to initially move into engagement with the innermost end of the anal canal so as to effectively lock the speculum into position during a colonic lavage operation.

Thus it will be appreciated by those skilled in the art that the embodiments described above provide a speculum which can be placed in the anal canal and lower rectum for the introduction of water or other liquid into the rectum, sigmoid colon and the remainder of the large intestine if desired; and which may further be employed for draining liquids and fecal matter out of the colon.

It will also be appreciated that the embodiments provide a speculum and control valve which are conformable for use in various colonic lavage apparatus to carry out either pressurecontrolled or timer-controlled fill and drain cycles in an effective and dependable manner.

It will be further appreciated that the described embodiments provide a speculum which will effectively minimize the abrasion, perforation or infection of the anal canal and rectum when employed in bowel care treatment devices.

It will be still further appreciated that the described embodiments provide a speculum which when inserted into the anal canal of a patient will encourage proper dilation and anal contraction while limiting the depth of penetration when inserted; and in the course of insertion and removal into and from the anal canal will minimize any danger of damage resulting from abrasion., perforation of mucosa or pulling down of hemorrhoids but will insure most complete and total elimination possible of the bowels when employed in colonic lavage operations.

It will be still yet further appreciated that the described embodiments provide a control valve which will automatically regulate filling and draining of the colon in response to the pressure differential of a liquid delivered from a liquid supply pump.

It is to be understood that while a preferred form of speculum and control valve have been set forth herein that various modifications and changes may be made without departing from the spirit and scope of the present invention as defined by the appended claims.

We claim:

1. In colonic lavage apparatus including a speculum for insertion into the anal canal of a patient for the bidirectional flow of fluid therethrough, said speculum comprising:

an elongated tubular body having a hollow interior and terminating at one end in a tapered leading end and at an opposite end in a tubular trailing end, said body having a maximum diameter adjacent to but rearwardly of said tapered leading end and a portion tapering rearwardly from said maximum diameter area, said tapered leading end being provided with at least one aperture communicating with the interior of said body, each said aperture having a rearward portion diverging forwardly for the greater length of each said aperture and having rounded edges surrounding said aperture; and an anal stop adjacent said trailing end of said body, said maximum diameter area located relatively near said leading end and away from said anal stop.

2. A colonic lavage apparatus according to claim 1, wherein said tapered leading end has a rounded, snubnosed tip, said tip formed in the shape of an ellipse taken as a quadrant of an ellipse rotated with displacement about a longitudinal axis of said body.

3. A colonic lavage apparatus according to claim 2, wherein there is provided a pair of said apertures diverging forwardly along said leading end, each having a diameter at its forward end corresponding to the inner diameter of said body.

4. A colonic lavage apparatus according to claim 3, wherein each said aperture has a forward end of semicircular configuration and provided with a rounded edge at said forward end which is flared outwardly from an inner surface of said leading end, said aperture including a rearwardly convergent end having rounded edges flared outwardly from an inner wall surface of said leading end.

5. A colonic lavage apparatus according to claim 4, wherein said body has an inner wall surface of uniform diameter along a substantial part of its length and an external wall surface defining said tapered leading end and said rearwardly tapered portion.

6. A colonic lavage apparatus according to claim 5, wherein said speculum is provided with an inflatable cuff disposed in surrounding relation to said body, and means communicating with the interior of said cuff for inflating said cuff to expand in an outward circumferential direction away from said body to hold said speculum in the anal canal of the patient.

7. A colonic lavage apparatus according to claim 6, wherein said cuff is composed of elastomeric material and is of tubular configuration having a pair of opposite ends, said opposite ends of said cuff being disposed in snugfitting, sealed engagement with axially spaced grooves in said body.

8. A colonic lavage apparatus according to claim 7, wherein said opposite ends of said cuff are in the form of O-rings, and said inflating means includes an air passage communicating with a recessed area of said body which opens outwardly into the interior of said cuff.

9. A colonic lavage apparatus according to claim 7 wherein said opposite ends of said cuff are rolled into a substantially O-ring shaped configuration, and one sidewall of each groove disposed inwardly of said opposite end is beveled so that each respective opposite end is tightly seated within each respective groove.

10. A colonic lavage apparatus according to claim 7, wherein said cuff has a differential thickness increasing from a forward end engaging one of said grooves to an opposite rearward end engaging the other of said grooves.

11. In colonic lavage apparatus, a speculum for insertion into the anal canal of a patient comprising:

an elongated thin-walled tubular body having an outer wall terminating at one end in a tapered leading end and at an opposite end in a tubular trailing end, a liquid delivery conduit communicating with said trailing end, said body having a maximum diameter area adjacent to but rearwardly of said tapered leading end and a portion tapering rearwardly from said maximum diameter area, said tapered leading end provided with diametrically opposed apertures forwardly of said maximum diameter area and having a rounded, snubnosed tip, each said aperture having a rearward portion diverging forwardly for the greater length of said aperture, said tip formed in the shape of an ellipse taken as a quadrant of an ellipse rotated with displacement about a longitudinal axis of said body; and an inflatable cuff disposed in surrounding relation to said portion of said body tapering rearwardly from said maximum diameter area, means communicating with the interior of said cuff for inflating said cuff to expand in an outward circumferential direction away from said body, the cuff having a differential thickness increasing from a forward end engaging a groove in said body to an opposite rearward end engaging a second groove in said body axially spaced from said first groove.

12. A colonic lavage apparatus including a speculum for insertion into the anal canal of a patient wherein the speculum comprises an elongated tubular body having a hollow interior and terminating at one end in a tapered leading end and at an opposite end in a tubular trailing end, said body having a maximum diameter area adjacent to but rearwardly of said tapered leading end and a portion tapering rearwardly from said maximum diameter area, and means communicating with the interior of said cuff for inflating said cuff to expand in an outward circumferential direction away from said body, the cuff being composed of elastomeric material and of tubular configuration having a pair of opposite ends, said opposite ends of said cuff being disposed in snug-fitting, sealed engagement with axially spaced grooves in said body.

13. A colonic lavage apparatus according to claim 12, wherein said opposite ends of said cuff are rolled into a substantially O-ring shaped configuration, and one sidewall of each groove disposed inwardly of said opposite end is beveled so that each respective opposite end is tightly seated within each respective groove.

* * * * *